United States Patent
Prakash et al.

(10) Patent No.: US 7,288,670 B2
(45) Date of Patent: Oct. 30, 2007

(54) SYNTHESIS OF N-[N-(3,3-DIMETHYLBUTYL)-L-α-ASPARTYL]-L-PHENYLALANINE 1-METHYL ESTER USING 3,3-DIMETHYLBUTYRALDEHYDE PRECURSORS

(75) Inventors: Indra Prakash, Hoffman Estates, IL (US); Kenneth E. Furlong, Evans, GA (US); Handley E. Jackson, III, North Augusta, SC (US)

(73) Assignee: The Nutrasweet Company, Chicago, IL (US)

( * ) Notice: Subject to any disclaimer, the term of this patent is extended or adjusted under 35 U.S.C. 154(b) by 307 days.

(21) Appl. No.: 10/834,933

(22) Filed: Apr. 30, 2004

(65) Prior Publication Data
US 2004/0236140 A1 Nov. 25, 2004

Related U.S. Application Data

(60) Provisional application No. 60/468,076, filed on May 6, 2003.

(51) Int. Cl.
*C07K 5/06* (2006.01)
(52) U.S. Cl. ....................................... 560/41
(58) Field of Classification Search ............ 560/41
See application file for complete search history.

(56) References Cited

U.S. PATENT DOCUMENTS

| | | | |
|---|---|---|---|
| 5,480,668 A | 1/1996 | Nofre et al. | 426/548 |
| 5,510,508 A | 4/1996 | Claude et al. | 560/41 |
| 5,728,862 A | 3/1998 | Prakash | 560/40 |
| 5,905,175 A | 5/1999 | Guo et al. | 568/490 |
| 6,423,864 B1 | 7/2002 | Prakash et al. | 560/41 |
| 6,548,096 B1 * | 4/2003 | Amino et al. | 426/548 |
| 6,642,406 B2 | 11/2003 | Prakash et al. | 560/40 |
| 6,720,446 B2 | 4/2004 | Scaros et al. | 560/40 |

FOREIGN PATENT DOCUMENTS

| | | |
|---|---|---|
| WO | 00/15656 | 3/2000 |
| WO | 01/02332 | 1/2001 |

OTHER PUBLICATIONS

Larkin D. R. Journal of Organic Chemistry 1990, 55, 1563-1568.*
T. W. Greene, et al., Protective Groups in Organic Synthesis, John Wiley & Sons, Inc., New York, chapter 4, pp. 175-179 and 212-217(1991).
K. B. Wiberg, et al., "Thermochemical Studies of Carbonyl Reactions. 2. Steric Effects in Acetal and Ketal Hydrolysis", J. Am. Chem. Soc., vol. 103, pp. 4473-4478 (1981).
Database Crossfire Beilstein Online, Beilstein Institute for Organic Chemistry, Frankfurt-Main, Germany, database accession No. 2810842 (RID) XP002293793, abstract, 1981.

* cited by examiner

*Primary Examiner*—Johann R. Richter
*Assistant Examiner*—Valenrod Yevgeny
(74) *Attorney, Agent, or Firm*—Fitzpatrick, Cella, Harper & Scinto

(57) ABSTRACT

N-[N-(3,3-dimethylbutyl)-L-α-aspartyl]-L-phenylalanine 1-methyl ester is produced by hydrogenation of L-α-aspartyl-L-phenylalanine 1-methyl ester and 3,3-dimethylbutyraldehyde produced in situ by the hydrolysis or cleavage of a 3,3-dimethylbutyraldehyde precursor. The production method is efficient and low cost, as compared with conventional N-[N-(3,3-dimethylbutyl)-L-α-aspartyl]-L-phenylalanine 1-methyl ester synthesis.

9 Claims, No Drawings

SYNTHESIS OF N-[N-(3,3-DIMETHYLBUTYL)-L-α-ASPARTYL]-L-PHENYLALANINE 1-METHYL ESTER USING 3,3-DIMETHYLBUTYRALDEHYDE PRECURSORS

This application claims the benefit of U.S. Provisional Application No. 60/468,076, filed May 6, 2003.

BACKGROUND OF THE INVENTION

1. Field of the Invention

This invention relates to the synthesis of N-[N-(3,3-dimethylbutyl)-L-α-aspartyl]-L-phenylalanine 1-methyl ester (neotame) using 3,3-dimethylbutyraldehyde precursors. This method of producing neotame is more simple and more economical than the conventional preparation of neotame.

2. Related Background Art

N-[N-(3,3-dimethylbutyl)-L-α-aspartyl]-L-phenylalanine 1-methyl ester (neotame) is a high potency dipeptide sweetener (about 8000× sweeter than sucrose) that has the formula

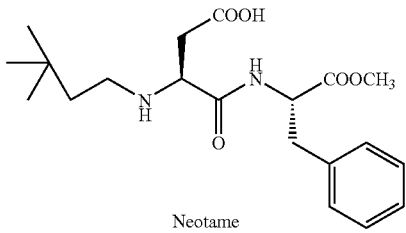

Neotame

The chemical synthesis of neotame is disclosed in U.S. Pat. Nos. 5,480,668, 5,510,508, 5,728,862 and WO 00/15656, the disclosure of each of which is incorporated by reference herein.

U.S. Pat. Nos. 5,510,508 and 5,728,862 describe the synthesis of neotame by hydrogenation of a mixture of aspartame and 3,3-dimethylbutyraldehyde with a catalyst such as Pd on carbon. This synthesis is represented by the following equation.

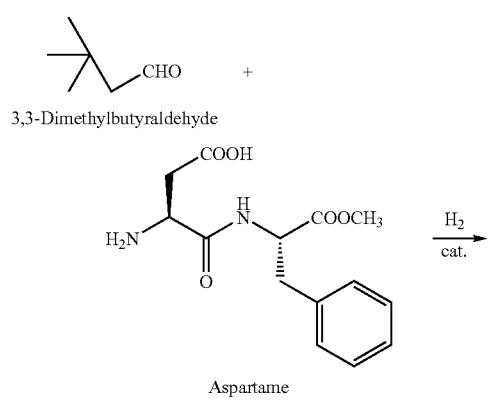

3,3-Dimethylbutyraldehyde

Aspartame

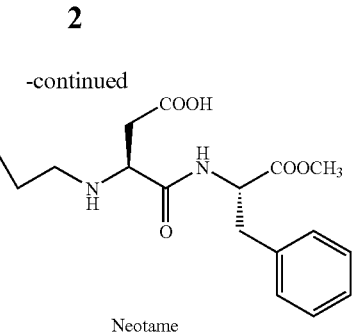

Neotame

The 3,3-dimethylbutyraldehyde used in this synthesis is typically produced from the bisulfite adduct of 3,3-dimethylbutyraldehyde by treatment with base, followed by distillation as described in U.S. Pat. No. 5,905,175, the disclosure of which is incorporated by reference herein. The above-noted neotame process requires the reaction of pure isolated aspartame with pure isolated aldehyde to produce neotame. However, it would be economically advantageous to use 3,3-dimethylbutyraldehyde precursors directly in neotame synthesis without having to first isolate 3,3-dimethylbutyraldehyde in order to economically and efficiently produce pure N-[N-(3,3-dimethylbutyl)-L-α-aspartyl]-L-phenylalanine 1-methyl ester.

SUMMARY OF THE INVENTION

The present invention relates to the efficient, low cost and high purity synthesis of N-[N-(3,3-dimethylbutyl)-L-α-aspartyl]-L-phenylalanine 1-methyl ester (neotame). According to one embodiment of the present invention, neotame is synthesized by reacting aspartame and 3,3-dimethylbutyraldehyde dimethyl acetal in a solvent or a mixture of solvents under hydrogenation conditions with a catalyst.

In a second embodiment of the present invention, neotame is synthesized by first hydrolyzing a bisulfite adduct of 3,3-dimethylbutyraldehyde with a base in a solvent or a mixture of solvents and then adding aspartame under hydrogenation conditions with a catalyst to produce neotame.

In a third embodiment of the present invention, neotame is synthesized by regenerating 3,3-dimethylbutyraldehyde from a hydrazone, semicarbazone or oxime of 3,3-dimethylbutyraldehyde by acidic hydrolysis or by oxidative cleavage in a solvent or a mixture of solvents and then adding aspartame under hydrogenation conditions with a catalyst to produce neotame.

In a fourth embodiment of the present invention, neotame is synthesized by hydrolyzing a trimer of 3,3-dimethylbutyraldehyde with an acid in a solvent or a mixture of solvents and then adding aspartame under hydrogenation conditions with a catalyst to produce neotame.

DETAILED DESCRIPTION

The present invention relates to the synthesis of N-[N-(3,3-dimethylbutyl)-L-α-aspartyl]-L-phenylalanine 1-methyl ester (neotame) by catalyzed hydrogenation of L-α-aspartyl-L-phenylalanine 1-methyl ester (aspartame) and 3,3-dimethylbutyraldehyde produced in situ by the hydrolysis or cleavage of a 3,3-dimethylbutyraldehyde precursor. More specifically, a precursor of 3,3-dimethylbutyraldehyde is hydrolyzed or cleaved to produce the aldehyde which is then used in situ to produce neotame, thereby eliminating the need to isolate 3,3-dimethylbutyraldehyde prior to its combination with aspartame. Precursors of 3,3-dimethylbutyraldehyde suitable for use in the present invention include 3,3-dimethylbutyraldehyde dimethyl acetal, the bisulfite adduct of 3,3-dimethylbutyraldehyde, the hydrazone, semicarbazone or oxime of 3,3-dimethylbutyraldehyde and the trimer of 3,3-dimethylbutyraldehyde.

According to the first embodiment of the present invention, N-[N-(3,3-dimethylbutyl)-L-α-aspartyl]-L-phenylalanine 1-methyl ester is synthesized by reacting aspartame and 3,3-dimethylbutyraldehyde dimethyl acetal (RR'=(OCH$_3$)$_2$) in a solvent or a mixture of solvents under hydrogenation conditions, i.e., in the presence of hydrogen, with a catalyst according to the following scheme:

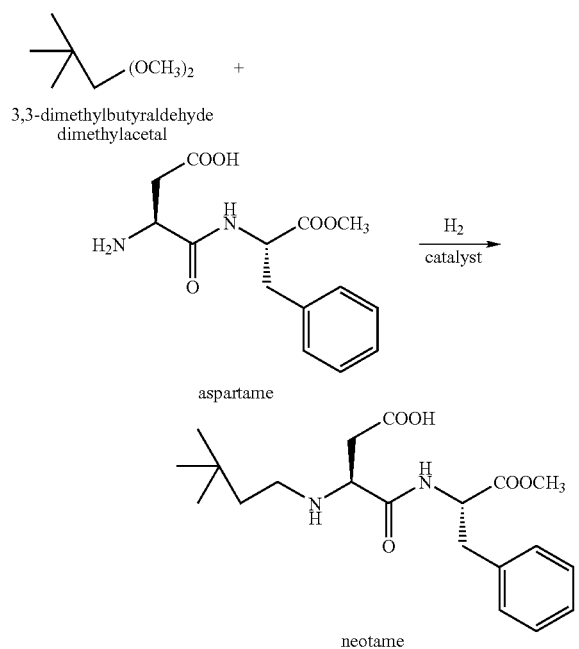

3,3-Dimethylbutyraldehyde dimethyl acetal suitable for use in the present invention may be obtained via the procedures outlined in "Protection for the Carbonyl Group", T. W. Greene, et al., Protective Groups in Organic Synthesis, 2d ed., John Wiley & Sons, New York, chapter 4, 1991. The 3,3-dimethylbutyraldehyde dimethyl acetal can be used in situ from its precursors in any known synthetic route (see above).

There is no need to hydrolyze the 3,3-dimethylbutyraldehyde dimethyl acetal prior to the addition to aspartame; however, if desired, the process of the first embodiment of this invention can be carried out in separate hydrolysis and hydrogenation steps. According to this invention, 3,3-dimethylbutyraldehyde is not isolated prior to the addition of aspartame; instead it is reacted in situ with aspartame to produce neotame. Generally the concentration of the 3,3-dimethylbutyraldehyde dimethyl acetal, and, in effect, the concentration of the 3,3-dimethylbutyraldehyde produced in situ, in the hydrogenation mixture is preferably in a range of about 0.90 to about 1.1, more preferably about 0.98 to about 1.0 on an equivalent molar ratio basis with aspartame.

According to the second embodiment of the present invention, neotame is synthesized by hydrolyzing a bisulfite adduct of 3,3-dimethylbutyraldehyde with a base in a solvent or a mixture of solvents to produce 3,3-dimethylbutyraldehyde in situ and then reacting the aldehyde with aspartame under hydrogenation conditions with a catalyst according to the following scheme:

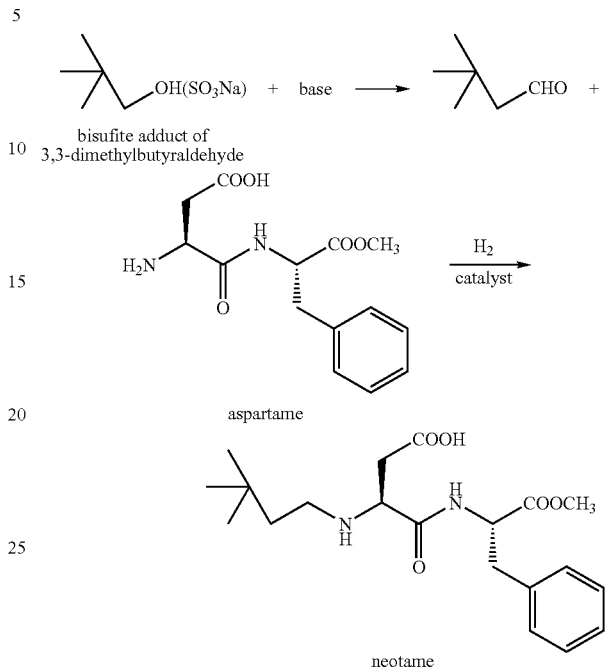

A bisulfite adduct of 3,3-dimethylbutyraldehyde (RR'=OH(SO$_3$Na)) suitable for use in the present invention may be obtained according to the procedure set forth in U.S. Pat. No. 5,905,175. The bisulfite adduct of 3,3-dimethylbutyraldehyde used in the present inventive process can be a wet cake, a dry cake or a solution in water. The bisulfite adduct of 3,3-dimethylbutyraldehyde can be used in situ from its precursors in any known synthetic route (see above).

Importantly, the bisulfite adduct of 3,3-dimethylbutyraldehyde must be hydrolyzed prior to the addition of aspartame. Again, however, according to this invention, 3,3-dimethylbutyraldehyde is not isolated prior to the addition of aspartame; instead the hydrolysis product of the bisulfite adduct of 3,3-dimethylbutyraldehyde is reacted in situ with aspartame to produce neotame. Generally the concentration of the bisulfite adduct used, and, in effect, the concentration of the 3,3-dimethylbutyraldehyde produced in situ, is preferably in a range of about 0.90 to about 1.1, more preferably about 0.98 to about 1.0 on an equivalent molar ratio basis with aspartame.

Bases suitable for use in the present invention include, without limitation, sodium bicarbonate, potassium bicarbonate, sodium carbonate, potassium carbonate, zinc oxide, zinc carbonate, magnesium oxide, calcium oxide, aluminum oxide, magnesium carbonate, calcium carbonate, monobasic potassium phosphate, dibasic potassium phosphate, tribasic potassium phosphate, monobasic sodium phosphate, dibasic sodium phosphate, tribasic sodium phosphate, ammonium phosphate, calcium phosphate, magnesium phosphate, ammonia, a tertiary amine, a secondary amine, a pyridine derivative, or a mixture thereof. Generally the amount of the base used is preferably in a range of about 1% to about 10%, more preferably about 1% to about 2% by weight based on the amount of the bisulfite adduct.

According to the third embodiment of the present invention, neotame is synthesized by regenerating 3,3-dimethylbutyraldehyde from a hydrazone, semicarbazone or oxime of 3,3-dimethylbutyraldehyde by acidic hydrolysis or oxidative cleavage in a solvent or a mixture of solvents to produce 3,3-dimethylbutyraldehyde in situ and then reacting the aldehyde with aspartame under hydrogenation conditions with a catalyst according to the following scheme:

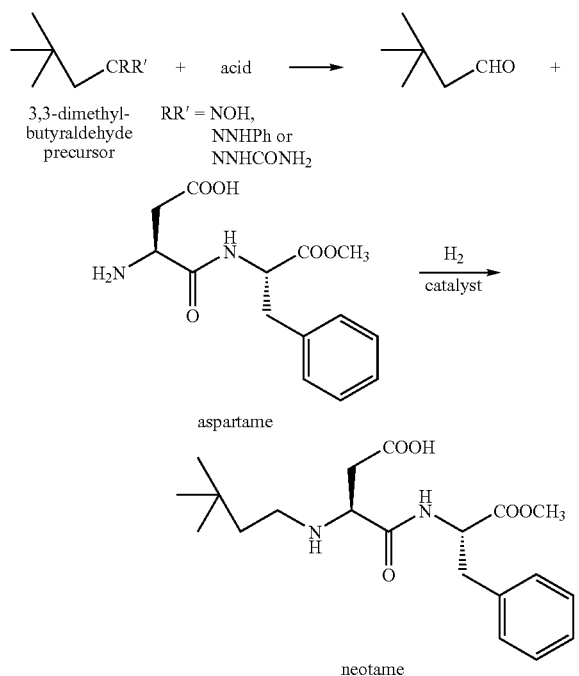

A hydrazone (RR'=NOH), semicarbazone (RR'=NNHCONH$_2$) or oxime (RR'=NNHPh) of 3,3-dimethylbutyraldehyde suitable for use in the present invention may be obtained via the procedures outlined in "Protection for the Carbonyl Group", T. W. Greene, et al., Protective Groups in Organic Synthesis, 2d ed., John Wiley & Sons, New York, chapter 4, 1991. The hydrazone, semicarbazone or oxime of 3,3-dimethylbutyraldehyde used in the present inventive process can be a wet cake or a dry cake. The hydrazone, semicarbazone or oxime of 3,3-dimethylbutyraldehyde can be used in situ from its precursors in any known synthetic route (see above).

Importantly, the hydrazone, semicarbazone or oxime of 3,3-dimethylbutyraldehyde must be hydrolyzed or cleaved prior to the addition of aspartame. Again, however, according to this invention, 3,3-dimethylbutyraldehyde is not isolated prior to the addition of aspartame; instead the hydrolysis or cleaved product of the hydrazone, semicarbazone or oxime of 3,3-dimethylbutyraldehyde is reacted in situ with aspartame to produce neotame. Generally the concentration of the hydrazone, semicarbazone or oxime of 3,3-dimethylbutyraldehyde used, and, in effect, the concentration of the 3,3-dimethylbutyraldehyde produced in situ, is preferably in a range of about 0.90 to about 1.1, more preferably about 0.98 to about 1.0 on an equivalent molar ratio basis with aspartame.

Acids suitable for use in the acid hydrolysis of this embodiment of the present invention include, without limitation, acetic acid, citric acid, nitrous acid and combinations thereof. Generally the concentration of the acid in the solvent is preferably in a range of about 1% to about 5%, more preferably about 1% to about 2% by weight of the amount of hydrazone, semicarbazone or oxime of 3,3-dimethylbutyraldehyde.

Oxidative agents suitable for use in the oxidative cleavage of this embodiment of the present invention include, without limitation, m-chloroperbenzoic acid, ozone, any hypervalent iodine agent such as sodium periodate, diacetoxyiodobenzene and iodosobenzene, and combinations thereof. Generally the concentration of the oxidative agent in the solvent is preferably in a range of about 0.5 to about 3, more preferably about 0.9 to about 1.1 on an equivalent molar ratio basis with the hydrazone, semicarbazone or oxime of 3,3-dimethylbutyraldehyde.

According to the fourth embodiment of the present invention, neotame is synthesized by hydrolyzing a trimer of 3,3-dimethylbutyraldehyde with an acid in a solvent or a mixture of solvents to produce 3,3-dimethylbutyraldehyde in situ and then reacting the aldehyde with aspartame under hydrogenation conditions with a catalyst according to the following scheme:

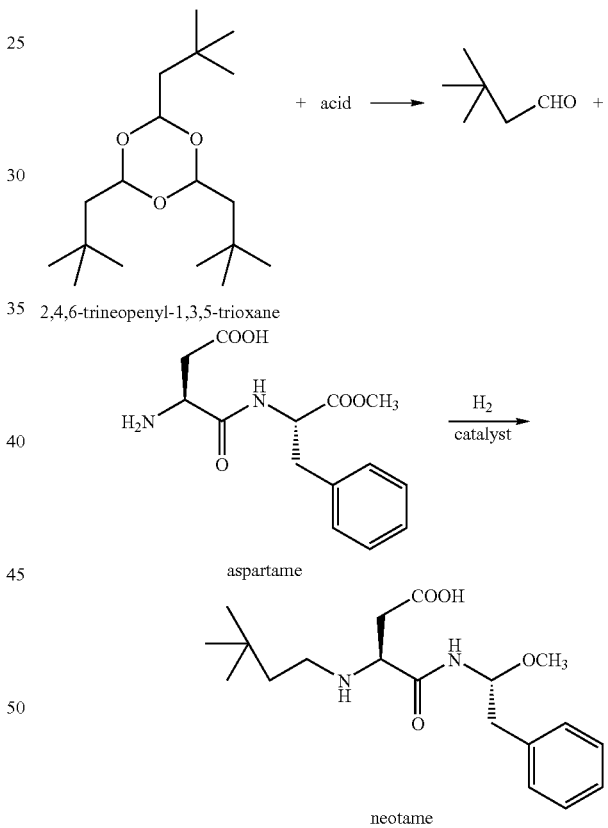

The trimer of 3,3-dimethylaldehyde suitable for use in the present invention may be obtained via the procedure set forth in Example 3 below or via any known synthetic route. The trimer can be used in situ from its precursors in any known synthetic route (see above).

Importantly, the trimer of 3,3-dimethylbutyraldehyde must be hydrolyzed prior to the addition of aspartame. Again, however, according to this invention, 3,3-dimethylbutyraldehyde is not isolated prior to the addition of aspartame; instead the hydrolysis product of the trimer of 3,3-dimethylbutyraldehyde is reacted in situ with aspartame to produce neotame. Generally the concentration of the trimer of 3,3-dimethylbutyraldehyde used is in a range of about 0.3 to about 1.1, more preferably about 0.33 to about 0.35 on an equivalent molar ratio basis with aspartame.

Acids suitable for use in this embodiment of the present invention include, without limitation, hydrochloric acid, acetic acid, sulfuric acid, and combinations thereof. Generally the concentration of the acid in the solvent is in a range of about 1% to about 20%, more preferably about 1% to about 10% by weight of the amount of trimer.

It is important to note that the hydrolysis or cleavage of the aldehyde precursor in each of the second, third and fourth embodiments of this invention can be accomplished via any known means. In addition, for each of these embodiments, an optional neutralization step may be required if an acid or a base is used in the hydrolysis or cleavage step. In particular, the pH of the solvent containing the aldehyde is preferably in a range of about 3 to about 7 prior to the addition of the aspartame for hydrogenation. If the pH of the solvent containing the aldehyde is not in such a range, then a neutralization step is required; neutralization can be accomplished by any known suitable means.

The remaining description of the parameters for the synthesis of neotame is applicable to each of the above-noted embodiments of the present invention.

Aspartame suitable for use in the present invention is commercially available or can be synthesized according to known methods. Further, pending U.S. patent application Ser. No. 09/859,438, filed May 18, 2001, is directed to the use of aspartame precursors in the synthesis of neotame; such aspartame precursors are also suitable for use in the present invention.

Solvents suitable for use in the present invention include, without limitation, ethanol, ethyl acetate, acetonitrile, dioxane, methanol, isopropanol, isobutyl methyl ketone, tetrahydrofuran, cyclohexane, toluene, dimethylformamide (DMF), water and mixtures thereof. The solvent can be added to a dry cake of a reactant, i.e., a 3,3-dimethylbutyraldehyde precursor or aspartame. Alternatively, the solvent may be used in situ in the formation of a 3,3-dimethylbutyraldehyde precursor, or it may be added to a reaction mixture.

The catalyst suitable for use in the present invention may be selected from catalysts based on palladium or platinum including, without limitation, platinum on activated carbon, palladium on activated carbon, platinum black or palladium black. Other catalysts include, without limitation, nickel on silica, nickel on alumina, Raney nickel, ruthenium black, ruthenium on carbon, palladium hydroxide on carbon, palladium oxide, platinum oxide, rhodium black, rhodium on carbon, rhodium on alumina and mixed catalysts as described in pending U.S. application Ser. No. 10/010,381 filed Mar. 28, 2002. The catalysts based on palladium or platinum are preferred.

The catalyst is present in an amount effective to produce neotame in an acceptable rate and yield. Generally, the weight ratio of catalyst (on a dry basis) to aspartame is about 0.01:1 to about 0.25:1, preferably about 0.10:1. It is important to note that about a 10% catalyst loading is required to minimize the undesirable yield of dialkylated aspartame.

The 3,3-dimethylbutyraldehyde and aspartame are typically combined in a substantially equivalent molar ratio, i.e., about 1:0.95 to 1:1. Excess molar amounts of aspartame are not preferred due to waste and cost. Higher molar amounts of the aldehyde precursor, and, in effect, the aldehyde are likely to lead to the generation of impurities.

The 3,3-dimethylbutyraldehyde produced in situ and aspartame are reacted for a time and at a temperature sufficient to produce neotame. Generally, the time sufficient to produce the aldehyde in situ ranges from about 0.5 to about 48 hours. Generally, the time sufficient to produce neotame ranges preferably from about 1 to about 24 hours, more preferably from about 6 to about 24 hours. Generally, the temperature sufficient to produce neotame according to the present invention ranges preferably from about 20° C. to about 60° C., more preferably from about 22° C. to about 40° C.

The reactions of the present invention are carried out in the presence of hydrogen. Generally, the pressure of the hydrogen ranges from about 5 psi to about 100 psi, preferably from about 30 psi to about 50 psi.

The present invention may also include additional steps. Such additional steps include, without limitation, catalyst removal, solvent concentration adjustment, holding, seeding, cooling (crystallization), and neotame isolation.

The catalyst may be separated by a variety of solid-liquid separation techniques that include, without limitation, the use of sparkler, crossflow, nutsche, basket, belt, disc, drum, cartridge, candle, leaf and bag filters. Furthermore, catalyst separation performance may be enhanced through the use of gravity, pressure, vacuum and/or centrifugal force. Additionally, the catalyst separation rate and removal efficiency may be enhanced through the use of any number of various filter media that include, without limitation, woven cloth fabrics, woven metal fabrics, porous metal substrates and synthetic or naturally occurring membranes. The separation device and media can be permanent, replaceable or disposable. The catalyst solid alone may be separated, or separation may be assisted by the use of porous cellulosic fiber or diatomaceous silica type filter aids, which are used as a media precoat and/or directly with a catalyst slurry. The separation device can be operated in an automated or manual mode for solid media washing, solid discharging and/or solid and media back flushing. The catalyst can be washed and discharged from the filter media using gas, liquid or mechanical means. The catalyst alone or catalyst with filter aid can be partially or totally recycled for used in subsequent hydrogenation reactions.

The reaction mixture, if water is present, may be held for a time and at a temperature sufficient to hydrolyze dialkylated imidazolidinone to $\alpha$-neotame and 3,3-dimethylbutyraldehyde. The reaction mixture is generally held for about 0.5-24 hours at a temperature of about 20-50° C. In a preferred embodiment of the present invention, the reaction mixture is held for about 2-4 hours.

Typically crystallization of neotame is accomplished by cooling the mixture to about 0-25° C., preferably to about 5-10° C., over the course of about 0.5-2 hours, preferably about 1-2 hours.

Seeding prior to or during crystallization can initiate a controlled crystal growth rate according to the present invention. Hence, the reaction mixture may optionally be seeded in an amount from 0.0001%-10%, by weight of the N-[N-(3,3-dimethylbutyl)-L-$\alpha$-aspartyl]-L-phenylalanine 1-methyl ester in the solution, preferably from 0.1% to 1% and most preferably from 0.1% to 0.5%. Seeding is typically performed at 25-35° C. and preferably at 28-30° C.

The reaction mixture or the solution containing neotame may be unstirred or stirred according to any embodiment of the present invention.

Crystallized neotame may be separated from the solvent solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the neotame solid-liquid separation device may be continuous, semi-continuous or in batch mode. The neotame solid may also be washed on the separation device using various liquid solvents, including, without limitation, water, methanol and mixtures thereof. The neotame solid can also be partially and totally dried on the separation device using any number of gases, including, without limitation, nitrogen and air, to evaporate residual liquid solvent. The neotame solid may be automatically or manually removed from the separation device using liquids, gases or mechanical means by either dissolving the solid or maintaining the solid form.

The neotame synthesized according to the present invention may be purified by any known method including, but not limited to, the following methods. U.S. Pat. No. 5,728,862 outlines a purification method by which neotame is precipitated out of an aqueous/organic solvent solution, wherein the aqueous/organic solvent solution has an amount of organic solvent of about 17% to about 30% by weight. U.S. Pat. No. 6,423,864 relates to methods of purifying neotame by crystallization in a variety of organic solvent/aqueous organic solvent mixtures; each of these methods involves the use of an organic solvent and water mixture and solvent distillation. Copending U.S. patent application Ser. No. 09/449,314, filed on Nov. 24, 1999, relates to methods of purifying neotame using chromatography.

The neotame synthesized according to the present invention is the monohydrate, which may be dried to produce an anhydrous form.

The crystallized and isolated neotame solid may be further purified by a variety of drying methods. Such methods are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer.

The above-described process of the present invention achieves a number of advantages as compared to conventional neotame synthetic routes. In particular, complicated processing steps to isolate 3,3-dimethylbutyraldehyde prior to combining it with aspartame are eliminated. On a manufacturing scale, this results in processing time savings, as well as a significant cost savings.

The examples which follow are intended as an illustration of certain preferred embodiments of the invention, and no limitation of the invention is implied.

EXAMPLE 1

Sodium bisulfite adduct of 3,3-dimethyl butylraldehyde (4.0 g), sodium hydrogen carbonate (2.2 g) and water (20 mL) were charged to a 50 mL round bottom flask. The mixture was heated to boiling and distilled to yield an azeotropic mixture of 3,3-dimethylbutyraldehyde and water (b. p. 82-85° C.). To this azeotropic mixture was charged L-aspartame (4.0 g, 13.5 mmol), methanol (50 mL) and 5% Pd/C (5%, 0.16 g). The mixture was hydrogenated at 30 psi/room temperature for 12-16 hours. The mixture was filtered through a Dicalite bed and the bed washed with methanol (5 mL). The methanol was reduced to half (25 mL) on a rotary evaporator under reduced pressure at room temperature and then water (30 mL) was added to it. The remaining methanol was distilled to a level of 15-30%. The mixture was left stirring at room temperature for 2-12 hours. The precipitated solid was filtered, washed with water (50 mL) and dried in a vacuum oven at 40° C./house vac/16 hours to get 2.8 g (56.%) of white solid (>97% pure by HPLC).

EXAMPLE 2

A slurry of L-aspartame (4.0 g, 13.5 mmol), dimethyl acetal of 3,3-dimethyl butylraldehyde (1.35 g, 13.5 mmol), methanol (50 mL) and 5% Pd/C (5%, 0.16 g) was hydrogenated at 30 psi/room temperature for 12-16 hours. The mixture was filtered through a Dicalite bed and the bed washed with methanol (5 mL). The methanol was reduced to half (25 mL) on a rotary evaporator under reduced pressure at room temperature and then water (30 mL) was added to it. The remaining methanol was distilled to a level of 15-30%. The mixture was left stirring at room temperature for 2-12 hours. The precipitated solid was filtered, washed with water (50 mL) and dried in a vacuum oven at 40° C./house vac/16 hours to get 3.9 g (73%) of white solid (>97% pure by HPLC).

EXAMPLE 3

3,3-Dimethylbutanal (10.0 g, 0.1 mol) was cooled to 0° C. and concentrated sulfuric acid (0.1 g) was added. Then, the reaction mixture was cooled to −30° C. (the reaction mixture solidified at this temperature) and kept for 2 hours at the same temperature. The mixture was warmed to 0° C. and diethyl ether (30 mL) was added. The solution was washed with saturated aqueous sodium bicarbonate (2×30 mL) and with water (2×30 mL). The extract was dried over magnesium sulfate and evaporated under reduced pressure (15 mm Hg, 40° C. water bath) to give colorless solid (8.8 g). The NMR analysis showed desired 2,4,6-trineopentyl-1,3,5-trioxane of 95% purity. The crude product was dissolved in methanol (20 mL) and filtered. Then water (20 mL) was slowly added to this solution and cooled to −20° C. for 1 hour. The colorless solid was separated, washed with water and dried in vacuum to give the pure product (7.5 g).

2,4,6-Trineopentyl-1,3,5-trioxane (3.3 g, about 10.7 mmol) was dissolved in toluene (3 mL) and 0.5 mL of 20% aqueous hydrochloric acid was added. The mixture was refluxed under nitrogen atmosphere for 1 hour (68-69° C.). The NMR analysis showed the only signals corresponding to 3,3-dimethylbutyraldehyde and benzene. The mixture was neutralized with sodium bicarbonate to pH=7 and the organic layer was transferred to the stirred suspension of aspartame (9.4 g, 31.9 mmol) and Pd/C (0.4 g) in methanol (150 mL) under nitrogen. Nitrogen was removed by hydrogen and the reaction mixture was vigorously stirred for 14 hours under light hydrogen pressure (<1 psi). Then, the mixture was filtered through Celite. The Celite layer was washed with methanol (25 mL) and evaporated under vacuum to half (about 80-90 mL), filtered and water (about 100 mL) was added to the residue. The mixture was gently evaporated under vacuum to remove methanol (without heating to keep low temperature of about 0-5° C.), and then kept at room temperature for 24 hours. The precipitate was filtered off, washed with water (30 mL) and dried under vacuum for 14 hours to give neotame (6.88 g, 57%).

While the invention has been described in terms of preferred embodiments and specific examples, those skilled in the art will recognize through routine experimentation that various changes and modifications can be made without departing form the spirit and scope of the invention. Thus, the invention should be understood as not being limited by the foregoing detailed description, but as being defined by the appended claims and their equivalents.

What is claimed is:

1. A process of synthesizing N-[N-(3,3-dimethylbutyl)-L-α-aspartyl]-L-phenylalanine 1-methyl ester comprising the step of:

reacting an admixture of L-α-aspartyl-L-phenylalanine 1-methyl ester and 3,3-dimethylbutyraldehyde dimethyl acetal in a solvent in the presence of a catalyst and hydrogen for a time and at a temperature sufficient to produce N-[N-(3,3-dimethylbutyl)-L-α-aspartyl]-L-phenylalanine 1-methyl ester.

2. The process according to claim 1, wherein the 3,3-dimethylbutyraldehyde dimethyl acetal is present in the admixture in a range of about 0.90 to about 1.1 on an equivalent molar ratio basis with L-α-aspartyl-L-phenylalanine 1-methyl ester.

3. The process according to claim 2, wherein the 3,3-dimethylbutyraldehyde dimethyl acetal is present in the admixture in a range of about 0.98 to about 1.0 based on an equivalent molar ratio basis with L-α-aspartyl-L-phenylalanine 1-methyl ester.

4. The process according to claim 1, wherein the catalyst is selected from the group consisting of platinum on activated carbon, palladium on activated carbon, platinum black, palladium black, nickel on silica, nickel on alumina, Raney nickel, ruthenium black, ruthenium on carbon, palladium hydroxide on carbon, palladium oxide, platinum oxide, rhodium black, rhodium on carbon and rhodium on alumina.

5. The process according to claim 1, wherein the weight ratio of catalyst on a dry basis to L-α-aspartyl-L-phenylalanine 1-methyl ester is from about 0.01:1 to about 0.25:1.

6. The process according to claim 1, wherein the solvent is selected from the group consisting of ethanol, ethyl acetate, acetonitrile, dioxane, isopropanol, methanol, isobutyl methyl ketone, tetrahydrofuran, cyclohexane, toluene, dimethylformamide, water and mixtures thereof.

7. The process according to claim 1, wherein the temperature sufficient to produce N-[N-(3,3-dimethylbutyl)-L-α-aspartyl]-L-phenylalanine 1-methyl ester is from about 20° C. to about 60° C.

8. The process according to claim 1, wherein the time sufficient to produce N-[N-(3,3-dimethylbutyl)-L-α-aspartyl]-L-phenylalanine 1-methyl ester is from about 1 hour to about 24 hours.

9. The process according to claim 1, wherein the pressure of the hydrogen is from about 5 psi to about 100 psi.

* * * * *